(12) United States Patent
Nishina et al.

(10) Patent No.: US 6,418,781 B1
(45) Date of Patent: Jul. 16, 2002

(54) SYSTEM FOR ANALYZING TRACE AMOUNTS OF IMPURITIES IN GASES

(75) Inventors: Akira Nishina; Tsutomu Kikuchi; Makoto Tanaka; Hidetoshi Yoshida; Tetsuya Kimijima, all of Tokyo (JP)

(73) Assignee: Nippon Sanso Corporation, Tokyo (JP)

( * ) Notice: Subject to any disclaimer, the term of this patent is extended or adjusted under 35 U.S.C. 154(b) by 0 days.

(21) Appl. No.: 09/445,413

(22) PCT Filed: Apr. 8, 1999

(86) PCT No.: PCT/JP99/01859
§ 371 (c)(1),
(2), (4) Date: Dec. 8, 1999

(87) PCT Pub. No.: WO99/53308
PCT Pub. Date: Oct. 21, 1999

(30) Foreign Application Priority Data
Apr. 9, 1998 (JP) .......................... 10-097970

(51) Int. Cl.$^7$ .................. B01D 15/08; F16K 31/02; H01J 49/40; G01N 30/02
(52) U.S. Cl. .................. 73/23.35; 73/31.03; 73/23.37; 210/656
(58) Field of Search .............. 73/23.35, 23.37, 73/31.03, 31.05; 250/339.07; 210/656

(56) References Cited

U.S. PATENT DOCUMENTS

| | | | | |
|---|---|---|---|---|
| 3,291,980 A | * | 12/1966 | Coates et al. ............. | 250/41.9 |
| 3,405,549 A | * | 10/1968 | Finley ...................... | 73/23.1 |
| 3,471,692 A | * | 10/1969 | Llewellyn et al. ......... | 250/41.9 |
| 3,563,083 A | * | 2/1971 | Benz ........................ | 73/23.1 |
| 3,566,674 A | * | 3/1971 | Talroze et al. ............ | 73/23.1 |
| 3,712,111 A | * | 1/1973 | Llewellyn .................. | 73/23.1 |
| 4,245,494 A | * | 1/1981 | Legendre et al. .......... | 73/23.1 |
| 4,641,541 A | * | 2/1987 | Sharp ....................... | 73/864.81 |
| 5,012,052 A | * | 4/1991 | Hayes ....................... | 250/288 |
| 5,083,450 A | * | 1/1992 | Grindstaff ................. | 73/23.25 |
| 5,411,707 A | * | 5/1995 | Hiatt ........................ | 422/68.1 |
| 5,457,316 A | * | 10/1995 | Cohen et al. ............. | 250/286 |
| 5,492,555 A | * | 2/1996 | Strunk et al. .............. | 95/86 |
| 5,872,306 A | * | 2/1999 | Arnold ...................... | 73/23.37 |
| 5,962,774 A | * | 10/1999 | Mowry et al. .............. | 73/23.37 |
| 5,970,804 A | * | 10/1999 | Bobbat, Jr. ................ | 73/863.12 |
| 6,125,689 A | * | 10/2000 | Graves et al. ............. | 73/23.37 |

FOREIGN PATENT DOCUMENTS

| | | |
|---|---|---|
| JP | 61-213655 | 9/1986 |
| JP | 6-34616 | 2/1994 |

\* cited by examiner

*Primary Examiner*—Hezron Williams
*Assistant Examiner*—David J. Wiggins
(74) *Attorney, Agent, or Firm*—Armstrong, Westerman & Hattori, LLP

(57) ABSTRACT

An analyzing apparatus for assaying various kinds of trace impurity contents in various kinds of high-purity gases, having an atmospheric pressure ionization mass spectrometer useful for determination of trace impurity contents in such high-purity gases on the ppb to sub ppb levels and a gas chromatograph integrated therewith, enabling high efficiency determination of trace impurity contents in high-purity gases. The analyzing apparatus having a gas chromatograph (8) and an atmospheric pressure ionization mass spectrometer (6), is provided with a system (10) for introducing a sample gas introduced from a sample gas introduction source directly to the atmospheric pressure ionization mass spectrometer (6); a system (14a, 14b) for introducing the sample gas via the gas chromatograph (8) to the atmospheric pressure ionization mass spectrometer (6); and a channel selector (11, 13, 15) for changing over the channel of the sample gas to either of these two systems.

3 Claims, 2 Drawing Sheets

SYSTEM FOR ANALYZING TRACE AMOUNTS OF IMPURITIES IN GASES

TECHNICAL FIELD

The present invention relates to an analyzing apparatus for assaying trace impurity contents in a gas, more particularly to such an analyzing apparatus for determining efficiently trace impurity contents in various kinds of high-purity gases on the ppb to sub ppb levels.

BACKGROUND ART

There have conventionally been utilized a gas chromatograph with a photoionization detector, a gas chromatograph mass spectrometer, a Fourier transform infrared spectrophotometer with a long light path gas cell, etc. when various kinds of impurity contents present on the ppb levels in high-purity gases employed in semiconductor manufacturing processes are assayed. Meanwhile, as monofunctional spectrometers, there have been utilized a yellow phosphorus emission type trace oxygen spectrometer, an emission spectrometer for assaying nitrogen in argon, various kinds of trace moisture meters, etc.

Recently, a sensitive gas analyzer called atmospheric pressure ionization mass spectrometer (APIMS) is utilized. This spectrometer is an evaluation analyzer indispensable for detection of impurity contents in high-purity gases as a spectrometer capable of measuring impurity contents on the ppb (1/1,000,000,000) to ppt (1/1,000,000,000,000) levels, and such atmospheric pressure ionization mass spectrometers are now used to determine impurity contents in nitrogen, argon, hydrogen or helium on the ppb to sub ppb levels.

However, there are some kinds of high-purity gases and impurity contents which are theoretically difficult to determine using the atmospheric pressure ionization mass spectrometer. It is theoretically difficult to perform sensitive determination of impurity contents, for example, hydrogen and carbon monoxide in nitrogen and most of impurity contents in oxygen. When determination of hydrogen in nitrogen is carried out using an atmospheric pressure ionization mass spectrometer, for those sample gases which contain water and methane as coexistent impurity contents, the protons (H) of water and methane are also detected in the mass number 29 ($N_2H$) detecting hydrogen, making it difficult to carry out accurate assay.

Meanwhile, carbon monoxide is determined by detecting the mass number 12 of C (carbon) atom, and coexistence of large amounts of methane ($CH_4$) and carbon dioxide ($CO_2$) each having a carbon atom makes it impossible to distinguish the carbon atom of carbon monoxide from those of such impurity contents. Accordingly, it has been a prerequisite of assay when carbon monoxide in nitrogen is actually determined that these coexistent impurity contents are as small as possible. However, since actual nitrogen gases contain such impurity contents as described above and in various levels, assay of impurity contents in nitrogen required an extra analyzer which can determine accurately hydrogen and carbon monoxide in addition to the atmospheric pressure ionization mass spectrometer.

Further, it is essential as a matter of fundamentals in the determination using an atmospheric pressure ionization mass spectrometer that the ionization potential of the major component gas is greater than those of impurity contents. However, the atmospheric pressure ionization mass spectrometer involves a theoretical problem that, when impurity contents in a high-purity oxygen gas are assayed, the ionization potential of the major component gas oxygen is small (12.6 eV), so that detectable impurity contents are limited to those which have small ionization potential values compared with that of oxygen, making it impossible to detect nitrogen, carbon monoxide, carbon dioxide, methane, etc. all having greater ionization potential values.

Accordingly, when such impurity contents are to be determined, analyzers each having a combination of means for separating impurity contents from oxygen gas using separation columns packed with various kinds of fillers and means for detecting impurity contents (photoionization detector, mass spectrometer, etc.), i.e., a gas chromatograph with a photoionization detector and a gas chromatograph mass spectrometer (GCMS), are employed under the present circumstances.

Further, as shown in FIG. 1, although there is devised a gas chromatograph atmospheric pressure ionization mass spectrometer using the atmospheric pressure ionization mass spectrometer (APIMS) 52 described above as detector for a gas chromatograph (GC) 51 aiming at sensitive assay, there are very few cases where it is employed practically. Meanwhile, referring to moisture content in oxygen, it is difficult to separate moisture on the ppb level using the gas chromatograph 51, so that a sensitive moisture meter 53 is generally connected, in addition to the gas chromatograph 51, to the atmospheric pressure ionization mass spectrometer via a selector valve 54 so as to determine moisture content separately. While there is also proposed a method for assaying moisture content in oxygen using the atmospheric pressure ionization mass spectrometer resorting to the cluster reaction, it had been difficult to apply this method to impurity contents other then moisture and hydrocarbons (ethane, propane, etc.).

As described above, while the atmospheric pressure ionization mass spectrometer is involved somehow or other in carrying out assays of impurity contents in high-purity gases, conditions under which a sample gas is introduced to the spectrometer varies between the case where determination is carried out using the atmospheric pressure ionization mass spectrometer only and the case where determination is carried out using additionally a gas chromatograph installed on the upstream side of the spectrometer. Accordingly, when the former determination is followed by the latter determination, the spectrometer is stopped, and after selection of the sample inlet for the gas chromatograph, the spectrometer is started up. Since determination is carried out after running-in of the spectrometer to provide a stable state, it takes considerable labor and time.

Further, as described above, considering that all of the impurity contents in various kinds of gases cannot be determined with high sensitivity (ppb to sub ppb) using the atmospheric pressure ionization mass spectrometer only, the above system involves inconveniences in that it must employ a plurality of analyzers, that adjustment of each analyzer is intricate and that the assay takes much time.

Therefore, it is an objective of the present invention to provide an analyzing apparatus for assaying trace impurity contents, integrated with an atmospheric pressure ionization mass spectrometer useful for determination of trace impurity contents on the ppb to sub ppb levels in various kinds of high-purity gases and a gas chromatograph, thus enabling assay of various kinds of impurity contents in various kinds of high-purity gases efficiently.

DISCLOSURE OF THE INVENTION

The analyzing apparatus for assaying trace impurity contents in a gas according to the present invention, which is provided with a gas chromatograph and an atmospheric pressure ionization mass spectrometer, comprises a system for introducing a sample gas introduced from a sample gas introduction source directly to the atmospheric pressure ionization mass spectrometer; a system for introducing the sample gas via the gas chromatograph to the atmospheric pressure ionization mass spectrometer; and channel selecting means for changing over the channel of the sample gas to either of these two systems.

Further, the channel selecting means is provided, as sample gas channels, with an assay passage for introducing the sample gas to the atmospheric pressure ionization mass spectrometer and a purge passage for exhausting the sample gas; a pressure control mechanism or a flow regulating mechanism, for equalizing the pressure of the sample gas when it flows through the assay passage and that of the sample gas when it flows through the purge passage, being installed in the purge passage or in the purge passage and an inlet channel or outlet channel of the atmospheric pressure ionization mass spectrometer.

According to the analyzing apparatus of the present invention, all the impurity contents in a sample gas can be determined by changing over the sample gas introduction passage to the desired one, and particularly when impurity contents in an oxygen gas are to be assayed, other analyzers need not be used. This not only eliminates the necessity of installing a plurality of analyzers and adjusting them but also saves the time and labor to be spent for the analysis. Further, those analyses which have conventionally be performed using the atmospheric pressure ionization mass spectrometer and other analyzers can be carried out using a unit of analyzing apparatus in a short time, and also high sensitivity and high accuracy determination on the ppb to sub ppb levels can be carried out. In addition, analyses can be performed in stable states by controlling pressure fluctuation and the like which can occur in channel selection.

BEST MODE FOR CARRYING OUT THE INVENTION

The present invention will be described more specifically referring to the attached drawings FIGS. 2 to 4.

Figure 1:
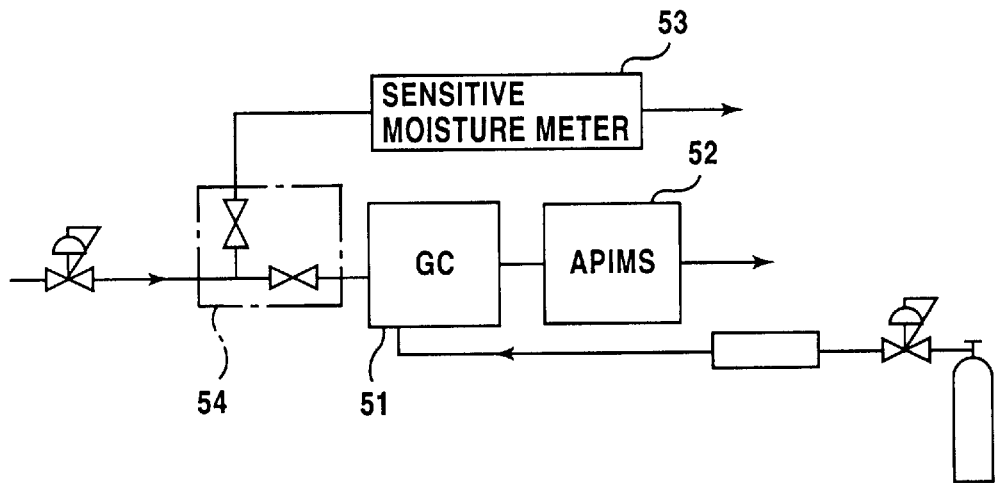
FIG. 1 is a system diagram showing an example of conventional analyzing apparatus.
Figure 2:
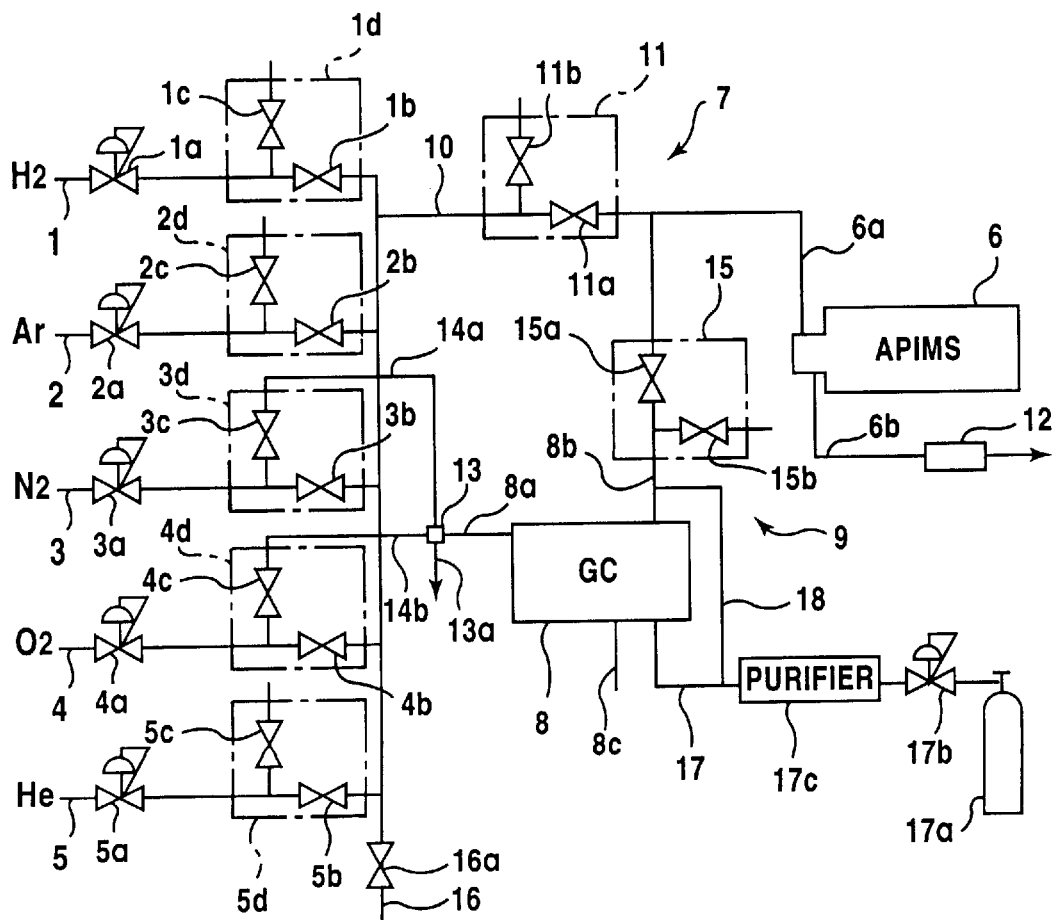
FIG. 2 is a system diagram showing the analyzing apparatus according to one embodiment of the present invention.

FIG. 2 is a system diagram showing the analyzing apparatus according to one embodiment of the present invention. This analyzing apparatus is for assaying trace impurity contents in five kinds of high-purity gases including hydrogen ($H_2$), argon (Ar), nitrogen ($N_2$), oxygen ($O_2$) and helium (He) and is provided with introduction passages 1, 2, 3, 4 and 5 for introducing the high-purity gases as sample gases respectively, a first assay system 7 for introducing the high-purity gases directly to an atmospheric pressure ionization mass spectrometer 6 and a second assay system 9 for introducing the high-purity gases to the atmospheric pressure ionization mass spectrometer 6 via a gas chromatograph 8.

The introduction passages 1, 2, 3, 4 and 5 are provided with pressure control valves 1a, 2a, 3a, 4a and 5a, and introduction selector valves 1d, 2d, 3d, 4d and 5d which are combinations of inlet valves 1b, 2b, 3b, 4b and 5b and purge valves 1c, 2c, 3c, 4c and 5c, respectively. The inlet valves 1b, 2b, 3b, 4b and 5b are connected parallelwise on the downstream sides to a first assay passage 10 constituting the first assay system 7.

The first assay passage 10 is provided with a first assay selector valve 11 containing a first assay valve 11a and a second assay valve 11b. The first assay valve 11a is connected on the downstream side to an inlet channel 6a of the atmospheric pressure ionization mass spectrometer 6. The atmospheric pressure ionization mass spectrometer 6 is provided in its outlet channel 6b with a mass flowmeter 12.

The nitrogen introduction passage 3 and the oxygen introduction passage 4 are provided with purge valves 3c and 4c which are connected respectively to second assay passages 14a and 14b communicating to a channel selector valve 13. These two passages 14a and 14b are changed over by the channel selector valve 13 to an inlet channel 8a of the gas chromatograph 8 or to a purge channel 13a. Meanwhile, the gas chromatograph 8 is provided in its outlet channel 8b with a second assay selector valve 15 containing a second assay valve 15a and a second purge valve 15b. The second assay valve 15a is connected on the downstream side to a passage located between the first assay valve 11a of the first assay passage 10 and the inlet channel 6a of the atmospheric pressure ionization mass spectrometer 6.

That is, the second assay system 9 consists essentially of the passages starting from the second assay passages 14a and 14b, through the channel selector valve 13, inlet channel 8a, gas chromatograph 8, outlet channel 8b and second assay selector valve 15 to the inlet channel 6a of the atmospheric pressure ionization mass spectrometer 6. The first assay selector valve 11 and the second assay selector valve 15 constitute a channel selector for selecting the first assay system 7 for introducing sample gases directly to the atmospheric pressure ionization mass spectrometer 6 or the second assay system 9 for introducing sample gases via the gas chromatograph to the atmospheric pressure ionization mass spectrometer 6.

To the first assay passage 10 is connected an exhaust passage 16 provided with an exhaust valve 16a for purging the passage when the sample gas is changed over to another. The gas chromatograph 8 is connected with a carrier gas introduction passage 17 for introducing a gas contained in a gas tank 17a through a pressure control valve 17b and a purifier 17c and is also provided with a make-up gas passage 18 which is extended from the carrier gas introduction passage 17 by-passing the gas chromatograph 8 and is connected to the outlet channel 8b.

When the high-purity gases are each analyzed by the atmospheric pressure ionization mass spectrometer 6, the inlet valve present in the introduction passage of the sample gas to be analyzed and the purge valve are opened and closed respectively, and the inlet valves in the other introduction passages are closed. This brings about a state where the sample gas to be analyzed flows into the first assay passage 10 of the first assay system 7. It is preferred that the purge valves in the other introduction passages are opened to allow flowing of the gases constantly so as to prevent contamination caused by outgassing of piping and the like as much as possible.

For example, when a hydrogen gas is to be analyzed, the inlet valve 1b and the purge valve 1c of the introduction passage 1 are opened and closed respectively, and the other inlet valves 2b, 3b, 4b and 5b are closed. Further, the first assay valve 11a and first purge valve 11b of the first assay selector valve 11 are opened and closed respectively, and the second assay valve 15a of the second assay selector valve 15 is closed. This brings about a state where a hydrogen gas adjusted to a predetermined pressure through the pressure control valve 1a and introduced through the introduction passage 1 flows through the inlet valve 1b, first assay passage 10, first assay valve 11a of the first assay selector valve 11 and through the inlet channel 6a into a measuring section of the atmospheric pressure ionization mass spectrometer 6, and after a predetermined assay is performed, the gas is exhausted from the outlet channel 6b and through the mass flowmeter 12.

When another gas such as argon is to be analyzed after analysis of hydrogen, the hydrogen inlet valve 1b and the argon inlet valve 2b are closed and opened respectively, and the open and closed postures of the purge valves 1c and 2c may be inverted. By selectively opening and closing the inlet valves 1b, 2b, 3b, 4b and 5b and the purge valves 1c, 2c, 3c, 4c and 5c successively, high-purity gases can be analyzed successively in the atmospheric pressure ionization mass spectrometer 6. While nitrogen and oxygen gases flowed through the purge valves 3c and 4c into the second assay passages 14a and 14b respectively, one is exhausted through the channel selector valve 13 into the purge channel 13a and the other is exhausted through an exhaust passage 8c of the gas chromatograph 8.

Meanwhile, in the case of analysis via the gas chromatograph 8, for example, in an analysis of a high-purity oxygen gas, it is necessary to assay first only the moisture content in the atmospheric pressure ionization mass spectrometer 6, as described above, and then to assay other impurity contents in the gas chromatograph 8. In such cases, after completion of the predetermined analysis of a high-purity gas in the atmospheric pressure ionization mass spectrometer 6, the assay system is changed over from the first assay system 7 to the second assay system 9 to carry out the analysis of the other impurity contents.

That is, the open and closed postures of the valves in the first assay selector valve 11 and in the second assay selector valve 15 are inverted to allow the gas from the second assay system 9 passed the gas chromatograph 8 to flow through the second assay valve 15a into the atmospheric pressure ionization mass spectrometer 6, and also the channel of the channel selector valve 13 is changed over to the oxygen side to allow oxygen in the second assay passage 14b to flow through the inlet channel 8a into the gas chromatograph 8.

Thus, after impurity contents in the oxygen gas are separated by the gas chromatograph 8, the resulting gas is introduced as carried by a carrier gas from the outlet channel 8b, through the second assay valve 15a and inlet channel 6a, into the atmospheric pressure ionization mass spectrometer 6, where those impurity contents other than moisture which cannot be assayed directly by the atmospheric pressure ionization mass spectrometer 6 are separated from the major component oxygen and assayed. Meanwhile, a deficiency in the amount of the gas flowing out of the gas chromatograph 8 for the amount required in the atmospheric pressure ionization mass spectrometer 6 is supplied from the make-up gas passage 18.

As described above, by connecting to the atmospheric pressure ionization mass spectrometer 6 a second sample gas introducing line (second assay system 9), containing the gas chromatograph 8, in addition to the sample gas introducing line (first assay system 7) employed in the ordinary direct method and by allowing a sample gas to flow through the second assay system 9, hydrogen and carbon monoxide in a nitrogen gas or carbon monoxide, hydrogen, methane, carbon dioxide, nitrogen, etc. in an oxygen gas, which can hardly be determined by the direct method, can be assayed. The other impurity contents in various kinds of gases can be determined using the first assay system 7 of the direct method. Thus, substantially all kinds of impurity contents to be determined in high-purity gases and the like can be assayed on the ppb to sub ppb levels. Further, since changing over to the desired sample gas can be carried out merely by opening and closing the valves, the assay condition can be changed over to a desired one easily in a short time.

Incidentally, as the carrier gas used in the gas chromatograph 8, while there may be used any desired gas such as helium, argon, nitrogen and hydrogen depending on the kind of major-component high-purity gas and on the kinds of impurity contents, helium is desirably used considering the following analysis in the atmospheric pressure ionization mass spectrometer 6. Further, as a separation column in the gas chromatograph 8, a desired column such as of zeolite and activated carbon can be used depending on the properties etc. of impurity contents.

The direct assay in the atmospheric pressure ionization mass spectrometer 6 and the assay via the gas chromatograph 8, as described above, can be repeated alternately and successively by incorporating a suitable sequencer and the like to effect inversion of the open and closed postures of the valves, enabling automatic assay of impurity contents in sample gases. While the sample gas switching time depends on the kind of gas, it is usually about 15 to 30 minutes.

Figure 3:
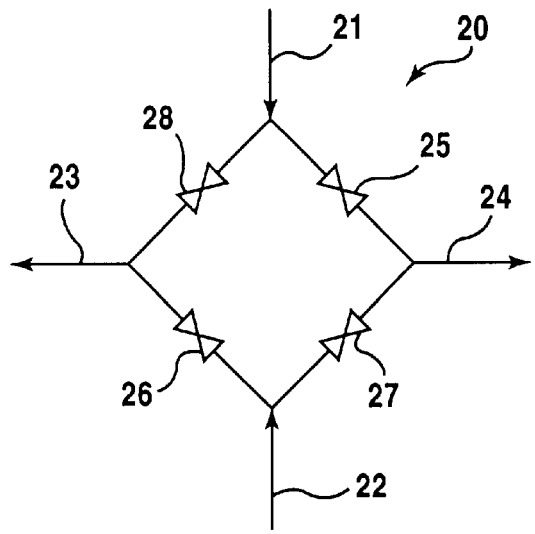
FIG. 3 is a system diagram showing another embodiment of the channel selecting means according to the present invention.

FIG. 3 is a system diagram showing another embodiment of the channel selector for selecting the system through which the sample gas is introduced into the atmospheric pressure ionization mass spectrometer 6. A channel selector 20 in this embodiment is an integrated valve formed by integrating the first assay selector valve 11 of the first assay system 7 and the second assay selector valve 15 of the second assay system 9 into one body, in which a first passage 21 from the first assay system 7, a second passage 22 from the second assay system 9, a purge passage 23 and an assay passage 24 to the atmospheric pressure ionization mass spectrometer 6 are connected by four valves 25, 26, 27 and 28 to form a rectangular piping as shown in FIG. 3.

In the channel selector 20 having the above structure, when the valves 25 and 26 are opened and the valves 27 and 28 are closed, the sample gas from the first passage 21 is allowed to flow through the valve 25 into the assay passage 24, whereas the sample gas from the second passage 22 is allowed to flow through the valve 26 into the purge passage 23. On the contrary, when the valves 27 and 28 are opened and the valves 25 and 26 are closed, the sample gas from the second passage 22 is allowed to flow through the valve 27 into the assay passage 24, whereas the sample gas from the first passage 21 is allowed to flow through the valve 28 into the purge passage 23.

Dead space can be minimized by using the integrated valve for the assay system selecting section, as described above, achieving reduction in the sample gas switching time, improvement of analysis accuracy, etc.

Figure 4:
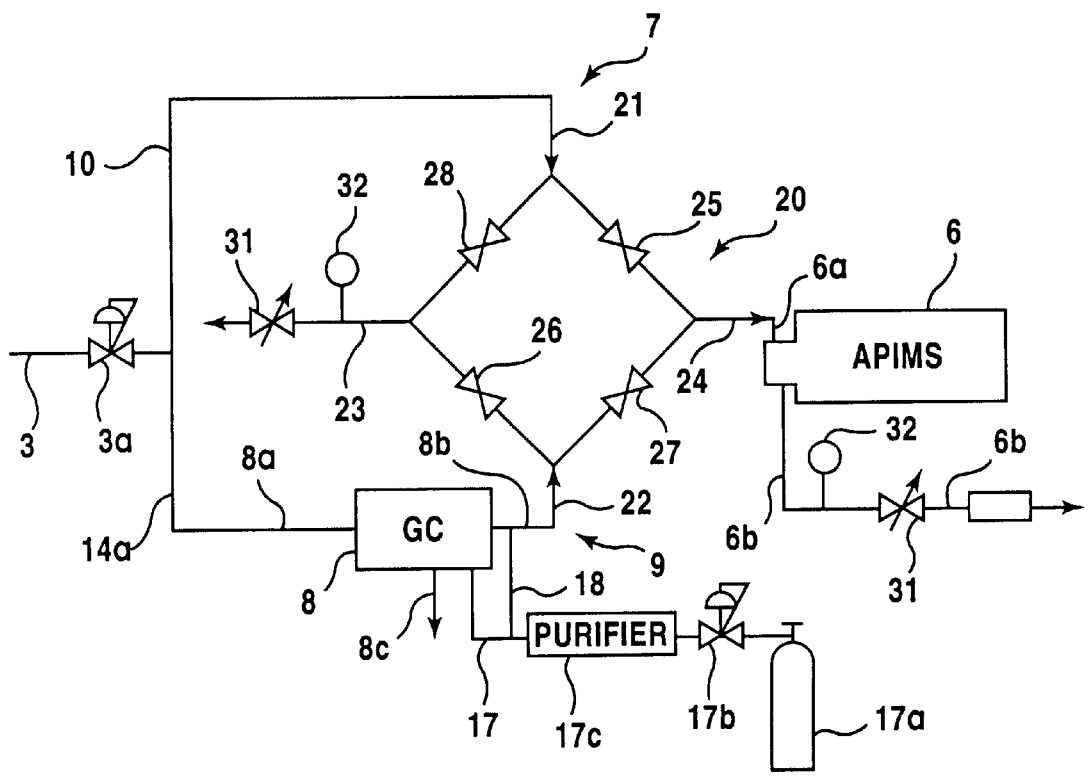
FIG. 4 is a system diagram showing an embodiment of the present invention, provided with means for preventing pressure fluctuation when the assay system is changed over to the other.

FIG. 4 is a system diagram showing an embodiment provided with means for preventing pressure fluctuation occurring when the assay system is changed over to the other, illustrating an introduction passage 3 for nitrogen analysis only as the introduction passage. First, the flow rate of the sample gas to be introduced to the atmospheric pressure ionization mass spectrometer 6, which is determined by the specifications of the atmospheric pressure ionization mass spectrometer 6, is usually several hundreds of milliliters to several liters per minute; while the flow rate of the carrier gas in the gas chromatograph 8 is usually 20 to 50 ml per minute.

Accordingly, a substantial amount of make-up gas must be added from the make-up gas passage 18 to the gas flowing out of the gas chromatograph 8. However, the make-up gas dilutes the impurity contents to be determined, so that the flow rate of the make-up gas should be minimized. In order to enhance sensitivity of the assay of impurity contents via the gas chromatograph 8, the amount of the sample gas to be introduced into the atmospheric pressure ionization mass spectrometer 6 is as small as possible, for example, 300 ml/min.

Since both the gas chromatograph 8 and the atmospheric pressure ionization mass spectrometer 6 are operated under atmospheric or higher pressure, it is not necessary to reduce the atmospheric or higher pressure to vacuum using a special interface as required in the ordinary gas chromatograph mass spectrometer. Accordingly, when an analysis is carried out using the gas chromatograph 8 and the atmospheric pressure ionization mass spectrometer 6 which are merely connected to each other, no special contrivance is required in connecting them, except that the make-up gas passage 18 is added.

However, in the system where the first assay system 7 for introducing a sample gas directly into the atmospheric pressure ionization mass spectrometer 6 and the second assay system 9 for introducing a sample gas via the gas chromatograph 8 into the atmospheric pressure ionization mass spectrometer 6 are used selectively, pressure fluctuation can occur when the system is changed over from the system 7 to the system 9 or vice versa. If such pressure fluctuation occurs, it is liable that air migrates through an ion source outlet of the atmospheric pressure ionization mass spectrometer 6 into the ion source to contaminate the ion source and that it takes a considerable time to reduce adsorbates such as moisture. In such cases, the purging with the sample gas takes much time.

In order to ensure prevention of such pressure fluctuation, it is necessary to equalize the sample gas pressure on the inlet sides of the channel selector 20, i.e., in the passages 21 and 22 of the systems 7 and 9, and also to equalize the pressure on the sample gas outlet sides, i.e. in the purge passage 23 and the assay passage 24, by adjusting the amount of make-up gas and the like.

While the pressure equalization as described above can be achieved by adjusting the length and diameter of the piping so as to equalize the piping resistance values in these sections, accurate pressure measuring means and pressure adjusting means are usually installed in close proximity to the inlet and outlet of the channel selector 20 so as to ensure rigid equalization. However, it can increase the possibility of causing contamination of the sample gas to install such means on the line, present on the upstream side of the atmospheric pressure ionization mass spectrometer 6, through which the sample gas passes and is not preferred in determination of ultramicro impurity contents.

Under such circumstances, as shown in FIG. 4, a pressure controller is installed in the introduction passage, and also flow regulating mechanisms 31 such as a needle valve, a mass flow controller and an adjuster and pressure gauges 32 are installed in the outlet channel 6b of the atmospheric pressure ionization mass spectrometer 6 and in the purge passage 23, thus preventing securely pressure fluctuation which can occur when the assay system is changed over to the other by the channel selector 20 as well as contamination of the sample gas. Further, according to this constitution, a high-pressure sample gas can be introduced to the atmospheric pressure ionization mass spectrometer 6, enabling assay of micro impurity contents with higher sensitivity.

The analyzing apparatus having the above constitution can achieve improvement in the assay sensitivity of hydrogen and carbon monoxide as impurity contents in nitrogen gas from the several ppb levels to the ppb to sub ppb levels. In addition, referring to the standard gas diluting apparatus necessary for calibration of impurity contents, one such apparatus may be present in one unit including the analyzing apparatus, and the analyzing apparatus can carry out accurate analyses, unlike the conventional system where a plurality of analyzers are used, since it can prevent errors attributed to instrumental errors which can occur when a plurality of calibrators are used.

Test Example

All the impurity contents in a high-purity nitrogen were determined using an analyzing apparatus having an introduction passage of the constitution as shown in FIG. 4. More specifically, an analysis was carried out by introducing the high-purity nitrogen as a sample gas having a predetermined pressure through the introduction passage 3 and the pressure control valve 3a and opening and closing the valves in the channel selector in a predetermined order.

First, the valve 25 of the channel selector 20 was opened, and the sample gas fed through the introduction passage 3 is introduced through the first assay passage 10 and the channel selector 20 directly to the atmospheric pressure ionization mass spectrometer 6 to determine oxygen, carbon dioxide, methane and moisture as impurity contents.

Next, the valve 27 of the channel selector 20 was opened, and the sample gas fed through the introduction passage 3 was introduced through the second assay passage 14a into the gas chromatograph 8, and after adjustment of the flow rate of the gas led out of the gas chromatograph 8 as carried on a carrier gas to a predetermined level by adding a make-up gas thereto, the resulting gas was introduced through the channel selector 20 to the atmospheric pressure ionization mass spectrometer 6 to carry out determination of hydrogen and carbon monoxide as impurity contents. Incidentally, a purified argon gas was used as the carrier gas in the gas chromatograph 8.

Consequently, the direct analysis gave the following results:

| | |
|---|---|
| oxygen | 0.4 ppb |
| carbon dioxide | 0.6 ppb |
| methane | 0.1 ppb |
| moisture | 4.0 ppb |

The analysis via the gas chromatograph 8 gave the following results:

| | |
|---|---|
| hydrogen | 2.5 ppb |
| carbon monoxide | 0.8 ppb |

What is claimed is:

1. An analyzing apparatus for assaying trace impurity contents in a gas which includes a gas chromatograph and an atmospheric pressure ionization mass spectrometer, the analyzing apparatus comprising:

a first system for introducing a sample gas introduced from a sample gas introduction source directly to the atmospheric pressure ionization mass spectrometer;

a second system for introducing the sample gas via the gas chromatograph to the atmospheric pressure ionization mass spectrometer;

a four-way block valve as channel selecting means for changing over a first channel of the sample gas to either of the first and second systems, wherein the valve is provided with, as additional sample gas channels, an assay passage for introducing the sample gas to the atmospheric pressure ionization mass spectrometer, a purge passage for exhausting the sample gas and four valves of the four-way block valve being opened and closed in mutual relation to when a first valve and a second valve are opened and a third valve and a fourth valve are closed, when the third valve and the fourth valve are opened and the first valve and the second valve are closed; when the first valve and the second valve are opened, the first system is connected to an inlet channel of the atmospheric pressure ionization mass spectrometer via the assay passage and the second system is connected to the purge passage; when the third valve and the fourth valve are opened, the second system is connected to an inlet channel of the atmospheric pressure ionization mass spectrometer via the assay passage and the first system is connected to the purge passage; and a pressure control mechanism or a flow regulating mechanism, for equalizing the pressure of the sample gas when it flows through the assay passage and that of the sample gas when it flows through the purge passage, being provided in the purge passage.

2. The analyzing apparatus for assaying trace impurity contents in a gas according to claim 1 wherein a second pressure control mechanism or a second flow regulating mechanism is provided in the inlet channel.

3. The analyzing apparatus for assaying trace impurity contents in a gas according to claim 1 wherein a third pressure control mechanism or a third flow regulating mechanism is provided in the outlet channel of the atmospheric pressure ionization mass spectrometer.

\* \* \* \* \*